(12) United States Patent
Zhang et al.

(10) Patent No.: US 11,073,505 B2
(45) Date of Patent: Jul. 27, 2021

(54) INTERNET-OF-THINGS BASED CROP GROWTH MONITORING DEVICE AND METHOD THEREOF

(71) Applicant: China Institute of Water Resources and Hydropower Research, Beijing (CN)

(72) Inventors: Baozhong Zhang, Beijing (CN); Zheng Wei, Beijing (CN); Songjun Han, Beijing (CN); Zhigong Peng, Beijing (CN)

(73) Assignee: CHINA INSTITUTE OF WATER RESOURCES AND HYDROPOWER RESEARCH, Beijing (CN)

( * ) Notice: Subject to any disclaimer, the term of this patent is extended or adjusted under 35 U.S.C. 154(b) by 243 days.

(21) Appl. No.: 16/536,321

(22) Filed: Aug. 9, 2019

(65) Prior Publication Data
US 2020/0363387 A1 Nov. 19, 2020

(30) Foreign Application Priority Data
May 13, 2019 (CN) .......................... 201910394935.5

(51) Int. Cl.
*A01M 1/22* (2006.01)
*G01N 33/00* (2006.01)
(Continued)

(52) U.S. Cl.
CPC ......... *G01N 33/0098* (2013.01); *A01M 1/223* (2013.01); *G01N 33/246* (2013.01);
(Continued)

(58) Field of Classification Search
CPC ............ G01N 33/0098; G01N 33/246; G01N 2033/245; G01N 21/84; G01N 21/01;
(Continued)

(56) References Cited

U.S. PATENT DOCUMENTS 7,152,468 B1 * 12/2006 Peterson ................. G01W 1/14
73/170.17
8,434,392 B1 * 5/2013 Lerner ................... G01B 21/14
82/1.11
(Continued)

FOREIGN PATENT DOCUMENTS

CN 204465750 U * 7/2015
CN 106614440 A 5/2017
(Continued)

*Primary Examiner* — Mahendra R Patel
(74) *Attorney, Agent, or Firm* — Bayramoglu Law Offices LLC (57) ABSTRACT

An Internet-of-Things-based crop growth monitoring device includes a plurality of monitoring mechanisms. Each monitoring mechanism includes a base and a support rod fixed on the base. The support rod is provided with an electric element installation casing formed by snap-fitting an upper conical cover and a lower conical cover. A component for driving a swing cantilever to rotate is provided on the support rod at a position near a lowermost surface of the upper conical cover. A plurality of distance measuring laser sensors are provided on the swing cantilever. A component for driving an ultra-high-definition camera to rotate is provided on the support rod at the section of the upper conical cover. The images captured by the ultra-high-definition camera is used to obtain the leaf growth situation of the crops, and the data collected by the distance measuring laser sensors is used to determine the plant height of the crops.

17 Claims, 3 Drawing Sheets

(51) Int. Cl.
*H04N 5/232* (2006.01)
*G01N 33/24* (2006.01)
*G06T 7/00* (2017.01)
*H04N 5/225* (2006.01)
*H04N 7/18* (2006.01)
*G01W 1/14* (2006.01)
*H02J 7/35* (2006.01)
*H02K 7/116* (2006.01)

(52) U.S. Cl.
CPC ......... *G06T 7/0004* (2013.01); *H04N 5/2253* (2013.01); *H04N 5/23299* (2018.08); *H04N 7/181* (2013.01); *G01N 2033/245* (2013.01); *G01W 1/14* (2013.01); *G06T 2207/20084* (2013.01); *G06T 2207/30128* (2013.01); *G06T 2207/30188* (2013.01); *H02J 7/35* (2013.01); *H02K 7/116* (2013.01)

(58) Field of Classification Search
CPC ... G01N 2021/8466; G01N 2021/0112; H04N 5/23299; H04N 5/2253; H04N 7/181; H04N 5/2252; H04N 7/185; H04N 5/2257; A01M 1/223; G06T 7/0004; G06T 2207/20084; G06T 2207/30128; G06T 2207/30188; G01W 1/14; H02J 7/35; H02K 7/116; G01B 11/02; G01B 11/0608; G01D 21/02; A01G 7/045; A01B 79/005; A01C 21/005; G06N 7/005; A04L 67/12
USPC .......................................................... 43/112
See application file for complete search history.

(56) References Cited

U.S. PATENT DOCUMENTS

| | | | | |
|---|---|---|---|---|
| 10,999,976 | B2* | 5/2021 | Lys | F28F 21/085 |
| 2009/0311925 | A1* | 12/2009 | Hine | B63H 25/04 440/13 |
| 2016/0223511 | A1* | 8/2016 | Koshnick | A01C 21/005 |
| 2016/0247082 | A1* | 8/2016 | Stehling | G06N 7/005 |
| 2018/0024271 | A1* | 1/2018 | Koch | G01W 1/02 702/3 |
| 2018/0160649 | A1* | 6/2018 | Hicks | A01K 29/005 |
| 2019/0150357 | A1* | 5/2019 | Wu | A01C 21/00 |
| 2019/0259108 | A1* | 8/2019 | Bongartz | A01C 21/005 |
| 2019/0312548 | A1* | 10/2019 | Fernandez | G01N 21/94 |
| 2020/0029488 | A1* | 1/2020 | Bertucci | G06T 7/70 |
| 2021/0029983 | A1* | 2/2021 | Deering | A01M 31/002 |
| 2021/0158041 | A1* | 5/2021 | Chowdhary | G05D 1/0246 |

FOREIGN PATENT DOCUMENTS

| | | | | |
|---|---|---|---|---|
| CN | 107421582 | A | * | 12/2017 |
| CN | 107421582 | A | | 12/2017 |
| CN | 207037436 | U | * | 2/2018 |
| CN | 207037436 | U | | 2/2018 |
| CN | 108680706 | A | | 10/2018 |
| CN | 109168535 | A | | 1/2019 |
| CN | 208331653 | U | * | 1/2019 |
| CN | 208331653 | U | | 1/2019 |
| CN | 208476281 | U | | 2/2019 |
| CN | 209442209 | U | * | 9/2019 |
| KR | 20020039733 | A | * | 5/2002 |

\* cited by examiner

INTERNET-OF-THINGS BASED CROP GROWTH MONITORING DEVICE AND METHOD THEREOF

CROSS REFERENCE TO THE RELATED APPLICATIONS

This application is based upon and claims priority to Chinese Patent Application No. CN 201910394935.5, filed on May 13, 2019, the entire contents of which are incorporated herein by reference.

TECHNICAL FIELD

The present invention relates to the technical field of crop monitoring, and in particular to an Internet-of-Things based (IoT-based) crop growth monitoring device and a method thereof.

BACKGROUND

As a top agricultural-producing country, China has widespread crop planting areas, and various researches targeting crop improvements are continually emerging. In order to properly recognize the growth stage of the crops and to take appropriate measures, it is of great importance to monitor the crops in real-time. The real-time monitoring is crucial especially for the trial-produce crops in the test field, so that the detailed data is obtained to be used as an experimental basis.

Up to now, the growth situation of crops is mostly monitored through the on-the-spot observation of technicians. This approach is high-intensity, time-consuming and laborious, and runs counter to the working efficiency improvement.

SUMMARY

The present invention provides an IoT-based crop growth monitoring device and a method thereof for monitoring the growth conditions of the crops to address the above-mentioned drawbacks in the prior art.

In order to achieve the above objective, the technical solution proposed by the present invention is as follows.

In the first aspect, an IoT-based crop growth monitoring device includes a plurality of crop monitoring mechanisms mounted in the field. Each crop monitoring mechanism includes a base and a support rod fixed on the base. A plurality of fixing elements obliquely extending downward and forming a fixing claw are fixedly mounted on the base. A plurality of soil sensors are fixed on the fixing elements.

An upper conical cover with an opening facing downward is fixed on an upper end of the support rod. A lower conical cover capable of sliding up and down relative to the support rod is movably mounted on the support rod below the upper conical cover. The lower conical cover is snap-fitted with the upper conical cover to form an electric element installation casing. A top surface of the support rod is connected to a solar cell panel having a top area larger than a maximum cross-sectional area of the electric element installation casing. A rainfall sensor and a light sensor are mounted on the top of the solar cell panel.

A first worm gear is mounted on the support rod at a position near the lowermost surface of the upper conical cover through a bearing. A mounting block is fixed on an upper surface of the first worm gear. A swing cantilever perpendicular to the support rod is fixed on the mounting block. A plurality of distance measuring laser sensors equidistantly arranged are mounted on a lower surface of the swing cantilever. A strip-shaped groove for holding the swing cantilever is provided on an edge of the lower conical cover. A second worm gear is mounted on the support rod at a position near a top surface of the upper conical cover through a bearing. A support block is fixed on an upper surface of the second worm gear. An ultra-high-definition camera is obliquely mounted on the support block through a connection rod, and a lowermost point of the ultra-high-definition camera is higher than an uppermost point of the swing cantilever.

A support plate is fixed on the support rod in the electric element installation casing. An accumulator battery, a first motor connected to the accumulator battery, a second motor and a first motor-driven push rod are placed on the support plate. A first worm and a second worm are respectively fixed on output shafts of the first motor and the second motor. The first worm is engaged with the first worm gear, and the second worm is engaged with the second worm gear. A free end of the first motor-driven push rod is fixedly connected to an inner surface of the lower conical cover. An uppermost point of the support plate for mounting the first motor-driven push rod is lower than a lowermost point of the swing cantilever.

The distance measuring laser sensors and the ultra-high-definition camera are all electrically connected to the accumulator battery. The solar cell panel is connected to the accumulator battery and a controller through a solar controller. The soil sensor, the rainfall sensor, the light sensor, the distance measuring laser sensor, the first motor, the second motor, the ultra-high-definition camera, and the accumulator battery are all connected to the controller located in the electric element installation casing. The controllers of all the crop monitoring mechanisms communicate with a server in a monitor room through a wireless network.

In the second aspect, a monitoring method for the IoT-based crop growth monitoring device is further provided, which includes:

S1. acquiring a current time, and determining whether the current time is a crop growth monitoring time point, if yes, starting up the first motor-driven push rod to drive a top surface of the lower conical cover to move until a position lower than the lowermost point of the swing cantilever, then go to step S2 and step S7 at the same time, otherwise, continue to perform step S1;

S2. starting the first motor to drive the swing cantilever to rotate by a predetermined angle, and collecting distances between the distance measuring laser sensors and crops by all the distance measuring laser sensors on the swing cantilever one time;

S3. determining whether a total rotation angle of the swing cantilever driven by the first motor is greater than or equal to 360°; if yes, go to step S4; otherwise, go back to step S2;

S4. calculating, by the controller, an average plant height of the crops according to all data sent back by the distance measuring laser sensors during a startup process of the first motor, and sending the average plant height of the crops to the server;

S5. determining, by the server, whether a difference between the average plant height uploaded by each controller and the height threshold is less than a predetermined threshold, if yes, retaining the average plant height, and going to step S6, otherwise, marking the plant height as abnormal, and going to step S17;

S6. using an average value of all retained average plant heights as a measured plant height of the crops when determinations for all the average plant heights uploaded by the controller are completed;

S7. controlling the first motor-driven push rod to drive the lower conical cover to continue to move downward until traveling over a predetermined distance;

S8. starting up the second motor to drive the ultra-high-definition camera to rotate by a predetermined angle; stopping the second motor; and starting up the ultra-high-definition camera to capture crop images;

S9. determining whether a total rotation angle of the ultra-high-definition camera driven by the second motor is greater than or equal to 360°, if yes, starting up the first motor-driven push rod to drive the lower conical cover to return back to an original position, and then going to step S10, otherwise, going back to step S8;

S10. sending, by the controller, all the crop images captured by the ultra-high-definition camera during a startup process of the second motor to the server;

S11. inputting, by the server, all the crop images into a three dimensional (3D) convolutional neural network for recognizing pests and diseases, a 3D convolutional neural network for recognizing yellow leaves, and a 3D convolutional neural network for recognizing a leaf area, respectively; and outputting types of the pests and diseases recognized from the crop images in presence of the pests and diseases, a confidence level of the crop images in presence of the yellow leaves, and a confidence level of leaf area of each crop image;

S12. when 30% of the crop images are in presence of the pests and diseases, go to step S13; and when the confidence level of 30% of the crop images is greater than the predetermined threshold, go to the step S14;

S13. reading an activity time and a preferred band of the peats according to the type of the corresponding pests in the crop images; sending the activity time and the preferred band of the peats to the controller; and controlling the insecticidal lamp by the controller to activate the light beads having the preferred band during the activity time of the pests;

S14. reading all salinity, humidity and PH values of soil collected by the soil sensors from a previous crop growth monitoring time point to a current crop growth monitoring time point to determine a cause of the yellow leaves of the crops;

S15. calculating an average confidence level of the leaf areas by using the confidence levels of the leaf areas of the crop images uploaded by the same controller; and determining whether the average confidence level of the leaf areas is greater than a predetermined confidence level, if yes, retaining the average confidence level of the leaf areas and go to step S16; otherwise, deleting the average confidence level of the leaf areas;

S16. considering the leaves of the crops to be in a normal condition when a number of the retained average confidence level of the leaf areas is greater than 70% of a total average confidence level of the leaf areas;

S17. determining whether a lodging phenomenon of the crops exists by the server according to the crop images of abnormal plant heights uploaded by the controller; and S18. obtaining a comprehensive growth condition of the crops at the current crop growth monitoring time point according to the measured plant height, a pest condition, a yellow leaf condition, the leaf area and the lodging phenomenon of the crops.

The present invention has the following advantages: the fixing claw provided by the present invention facilitates the insertion of the base into the field, and provides places to attach the soil sensors, so that the soil sensors can be rapidly distributed in the field.

With the collaboration of the first motor, the first worm and the first worm gear, the plurality of distance measuring laser sensors are driven to rotate within a certain range and to collect the heights of the crops in the different ranges, so as to achieve the accurate collection of the plant heights of the crops.

In the present invention, the upper conical cover and the lower conical cover are snap-fitted to form the electric element installation casing, and the electric elements can be sealed in the casing, thereby improving the safety of the electric elements arranged in the monitoring mechanisms in the field. The images captured by the high-definition camera can be used to analyze the growth situation of the crop leaves, and whether the lodging and the pest attack occur in the crops.

The first motor-driven push rod is used to drive the lower conical cover to move downward along the support rod to make the visual field of the high-definition camera located in the electric element installation casing not be obstructed. With the collaboration of the second motor, the second worm gear and the second worm, the high-definition camera is rotated relative to the support rod, so as to further enlarge the collection range of the crops during each monitoring and thus achieving the purpose of more accurate monitoring.

The reference numerals in the figures are described below: 1, base; 11, fixing element; 12, soil sensor; 2, support rod; 21, bearing; 22, first worm gear; 221, mounting block; 23, swing cantilever; 231, distance measuring laser sensor; 24, second worm gear; 241, support block; 25, connection rod; 26, ultra-high-definition camera; 27, spherical hinge;

3, electric element installation casing; 31, upper conical cover; 32, lower conical cover; 321, strip-shaped groove; 33, support plate; 34, accumulator battery; 35, first motor; 351, first worm; 36, second motor; 361, a second worm; 37, first motor-driven push rod; 38, second motor-driven push rod; 39, third motor-driven push rod;

4, solar cell panel; 41, rainfall sensor; 42, light sensor; 5, controller; 6, insecticidal lamp; 61, connection rod; 62, circular base; 63, lamp cover; 64, glass lampshade; 65, high-voltage electric fence; 66, cylindrical circuit board; 661, annular circuit board; 6611, light bead.

DETAILED DESCRIPTION OF THE EMBODIMENTS

The embodiments of the present invention are described hereinafter, so that those skilled in the art can readily understand the present invention. However, it should be noted that the present invention is not limited to the scope defined by the embodiments. For those of ordinary skill in the art, all the variations, if falling within the spirit and scope of the present invention defined and determined by the appended claims, are considered to be obvious over the present invention. All inventions derived from the conception of the present invention are covered by the scope of the present invention.

Figure 1:
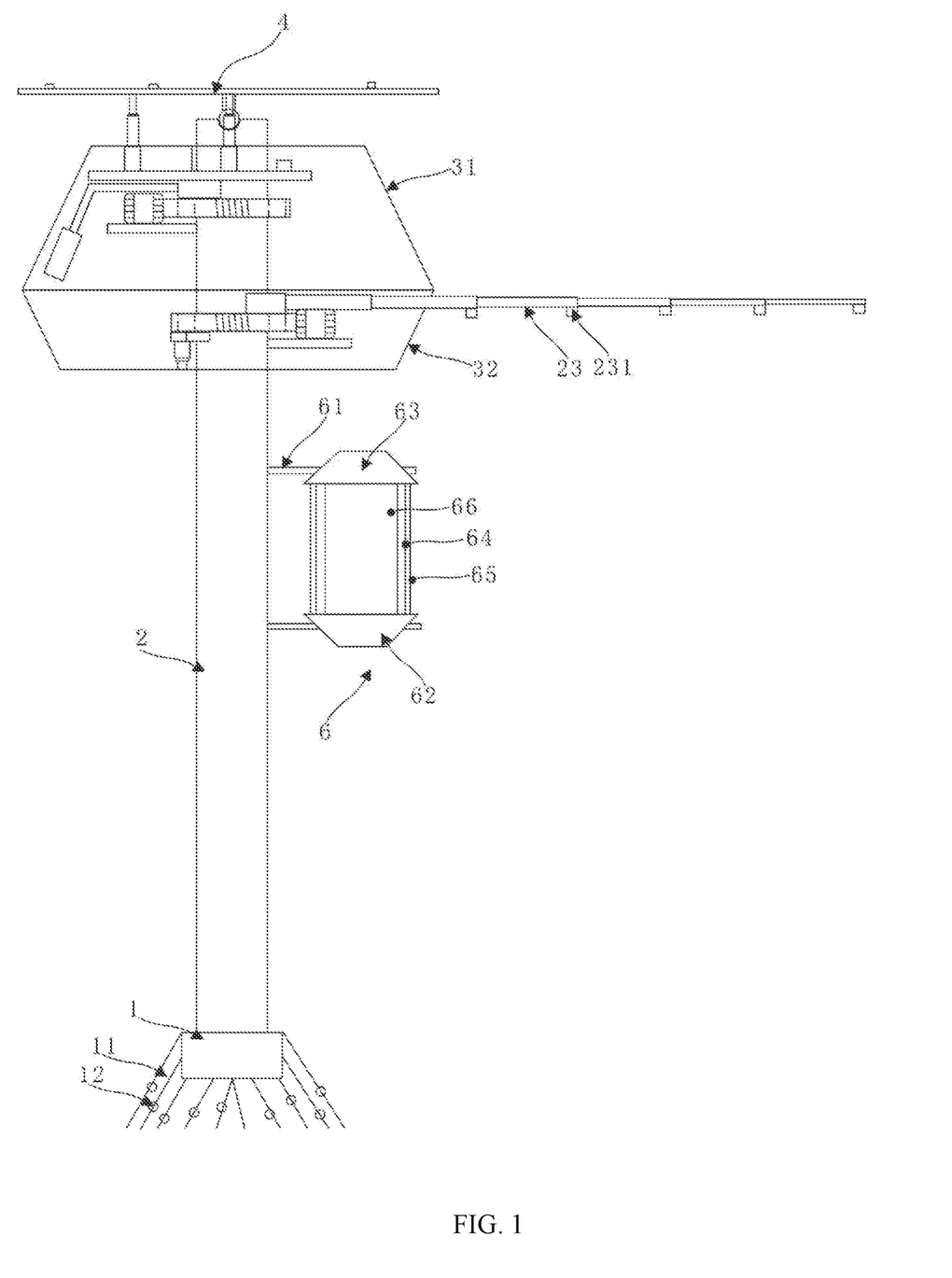
FIG. 1 is a structural schematic diagram showing an IoT-based crop growth monitoring device.
Figure 2:
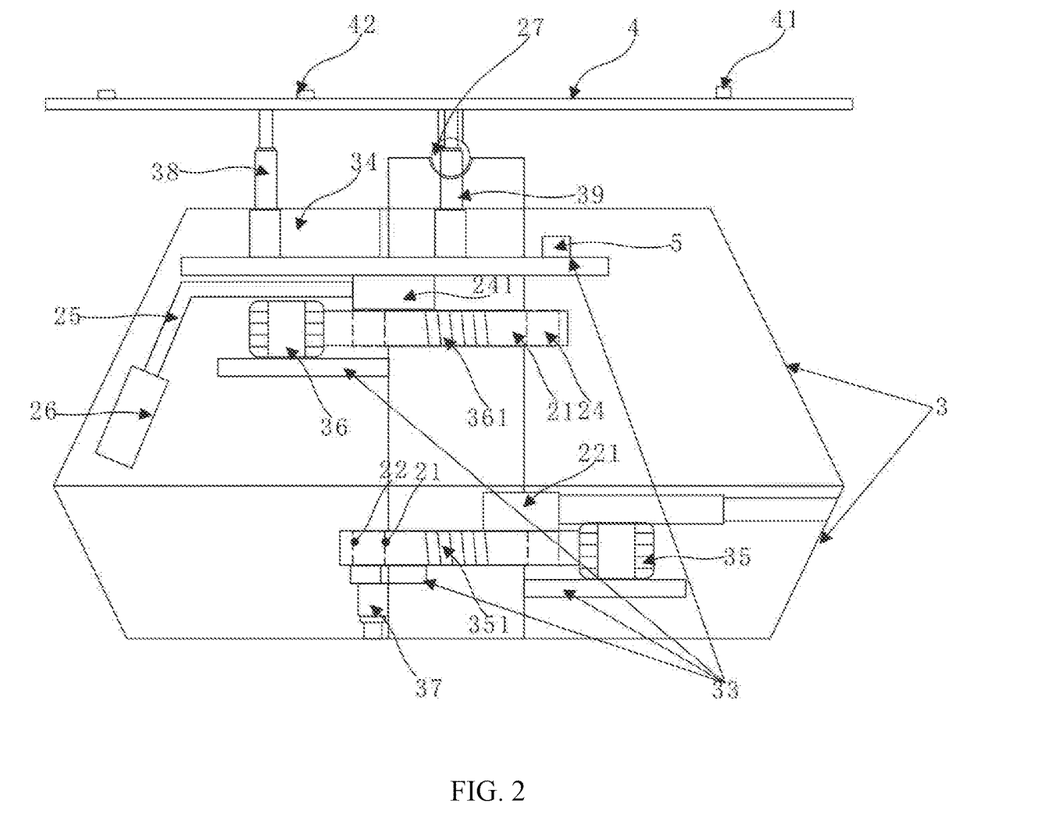
FIG. 2 is a partially enlarged view of FIG. 1.

As shown in FIG. 1 and FIG. 2, the IoT-based crop growth monitoring device of the present embodiment includes a plurality of crop monitoring mechanisms installed in the field. Each crop monitoring mechanism includes the base 1 and the support rod 2 fixed on the base 1. The plurality of fixing elements 11 obliquely extending downward and forming a fixing claw are fixedly mounted on the based 1. The plurality of soil sensors 12 are fixed on the fixing elements 11.

In practice, preferably, the soil sensors 12 include the soil salt content sensor, the pH probe, and the humidity sensor, which are electrically connected to the controller 5. By configuring the soil salt content sensor, the pH probe and the humidity sensor, the collected soil information can be sent to the server for storage through the controller 5. By comparing the collected soil information with the soil salt content reference value, the PH reference value and the humidity reference value stored in the serve, the server determines whether the crops are under nutrient and water deficient or not and reminds the administrator of timely supplementing the crops with the required substances according to the comparison result.

The upper conical cover 31 having an opening facing downward is fixed on the upper end of the support rod 2. The lower conical cover 32 capable of sliding up and down relative to the support rod 2 is movably mounted on the support rod 2 below the upper conical cover 31, wherein the lower conical cover 32 is provided with a mounting hole for the support rod 2 to pass through, and the diameter of the mounting hole is slightly larger than the diameter of the support rod 2.

The lower conical cover 32 is snap-fitted with the upper conical cover 31 to form the electric element installation casing 3. The solar cell panel 4 having a top surface area larger than the largest cross-sectional area of the electric element installation casing 3 is connected to the top surface of the support rod 2. The rainfall sensor 41 and the light sensor 42 are installed on the top surface of the solar cell panel 4.

Due to the distinctive size arrangement of the solar cell panel 4, the solar cell panel 4 arranged horizontally can completely shelter the electric element installation casing 3. In this way, when there is a rainfall, the solar cell panel 4 can protect the electric element installation casing from the rain, thereby protecting the electric elements inside the electric element installation casing 3.

Figure 3:
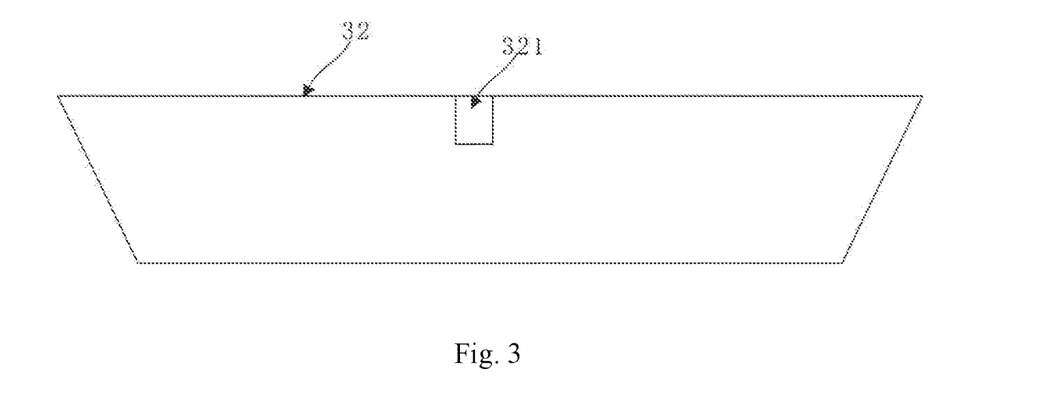
FIG. 3 is a side view of the lower conical cover.

As shown in FIG. 1 to FIG. 3, the first worm gear 22 is mounted on the support rod 2 at the position near the lowermost surface of the upper conical cover 31 through the bearing 21. The mounting block 221 is fixed on the upper surface of the first worm gear 22. The swing cantilever 23 perpendicular to the support rod 2 is fixed on the mounting block 221. The plurality of distance measuring laser sensors 231 arranged equidistantly are installed on the lower surface of the swing cantilever 23. The strip-shaped groove 321 for holding the swing cantilever 23 is provided at the edge of the lower conical cover 32. The width of the strip-shaped groove 321 is greater than the maximum of the width of the swing cantilever and the width of the distance measuring laser sensor 231.

By configuring the strip-shaped groove 321, when the lower conical cover 32 is snap-fitted with the upper conical cover 31, the upper surface of the lower conical cover 32 and the lower surface of the upper conical cover 31 can come in complete contact with each other, so as to avoid leaky joint between the lower conical cover 32 and the upper conical cover 31 under the presence of the swing cantilever 23, and thus affecting the protection of the electric elements in the electric element installation casing 3.

The second worm gear 24 is mounted on the support rod 2 at the position near the top surface of the upper conical cover 31 through bearing 21. The support block 241 is fixed on the upper surface of the second worm gear 24. The ultra-high-definition camera 26 is obliquely mounted on the support block 241 through the connection rod 25. The lowermost point of the ultra-high-definition camera 26 is higher than the uppermost point of the swing cantilever 23.

Due to the distinctive arrangement of the relative position between the ultra-high-definition camera 26 and the swing cantilever 23, the ultra-high-definition camera 26 is prevented from colliding with the swing cantilever 23 during rotation of the ultra-high-definition camera 26, so as to avoid influences on the image acquisition of crops and damages to the costly ultra-high-definition camera 26 due to collision.

The support plate 33 is fixed on the support rod 2 in the electric element installation casing 3. The accumulator battery 34, the first motor 35 connected to the accumulator battery 34, the second motor 36 and the first motor-driven push rod 37 are placed on the support plate 33. The first worm 351 and the second worm 361 are respectively fixed on the output shafts of the first motor 35 and the second motor 36. The first worm 351 is engaged with the first worm gear 22, and the second worm 361 is engaged with the second worm gear 24. The free end of the first motor-driven push rod 37 is fixedly connected to the inner surface of the lower conical cover 32. The uppermost point of the support plate for mounting the first motor-driven push rod 37 is lower than the lowermost point of the swing cantilever 23.

With the arrangement of the relative position of the first motor-driven push rod 37 and the swing cantilever 23, the rotation center of the swing cantilever 23 is higher than the first motor-driven push rod 37, so that the first motor-driven push rod 37 does not collide with the swing cantilever 23 during rotation of the swing cantilever 23, and the influences on the service life of the elongated swing cantilever 23 is avoided.

The four support plates 33 are mounted on the support rod 2 in the electric element installation casing 3 from top to bottom. Specifically, the second motor-driven push rod 38, the third motor-driven push rod 39, the accumulator battery 34 and the controller 5 are all mounted on the first support plate. The second motor 36 is mounted on the second support plate. The first motor-driven push rod 37 is mounted on the third support plate. The first motor is mounted on the fourth support plate.

The distance measuring laser sensor 231 and the ultra-high-definition camera 26 are both electrically connected to the accumulator battery 34. The solar cell panel 4 is connected to the accumulator battery 34 and the controller through the solar controller. The soil sensor 12, the rainfall sensor 41, the light sensor 42, the distance measuring laser sensor 231, the first motor 35, the second motor 36, the ultra-high-definition camera and the accumulator battery 34 are all connected to the controller 5 located inside the electric element installation casing 3. The controllers 5 of all the crop monitoring mechanisms communicate with the server in the monitor room through the wireless network.

When the distance measuring laser sensor 231 is used to collect the distances between the crops and the distance measuring laser sensor 231, first the first motor-driven push rod 37 is started to drive the top surface of the lower conical cover 32 to move until reaching the position below the lowermost point of the swing cantilever 23. After that, the first motor 35 is started to drive the swing cantilever 23 to rotate. For each time the swing cantilever 23 is rotated by a predetermined angle, the distance measuring laser sensor 231 is controlled to collect the height between the crops and the distance measuring laser sensor 231 for one time, and upload the height information to the controller 5.

When using the ultra-high-definition camera 26, first the first motor-driven push rod 37 is started to drive the lower conical cover 32 to move downward. After the lower conical cover 32 descends a predetermined distance, the ultra-high-definition camera 26 extends out of the closed electric element installation casing 3. Then, the second motor 36, the second worm gear 24 and the second worm 361 are started to work collaboratively and drive the ultra-high-definition camera 26 to move in circles. During the movement, for each time the ultra-high-definition camera 26 is rotated by a predetermined angle, the image of the crops is captured for one time.

As shown in FIG. 1 and FIG. 2, the solar cell panel 4 is movably mounted on the top end of the support rod 2 through the spherical hinge 27. The second motor-driven push rod 38 and the third motor-driven push rod 39 are fixed on the support plate 33 inside the electric element installation casing 3. The connection lines between the second motor-driven push rod 38 and the support rod 2, and between the third motor-driven push rod 39 and the support rod 2 are perpendicular to each other. The free ends of the second motor-driven push rod 38 and the third motor-driven push rod 39 both protrude out of the upper conical cover 31 and are connected to the solar cell panel 4 by the spherical hinge. Moreover, when the solar cell panel 4 is placed horizontally, the second motor-driven push rod 38 and the third motor-driven push rod 39 are in the stretched-out state.

With the arrangement of the second motor-driven push rod 38 and the third motor-driven push rod 39, the second motor-driven push rod 38 and the third motor-driven push rod 39 work collaboratively with the spherical hinge 27 to drive the solar cell panel 4 to tilt and expose to the sun, so that the solar cell panel can sufficiently capture the energy from the sun.

Figure 4:
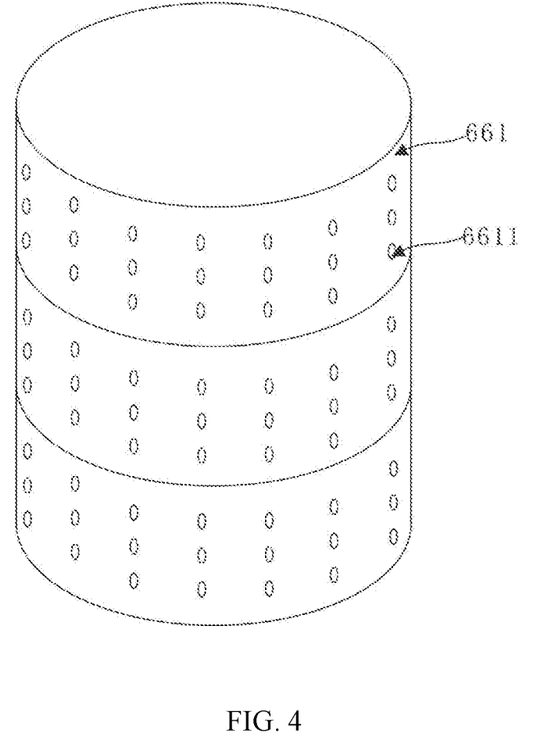
FIG. 4 is a perspective view of a cylindrical circuit board.

As shown in FIG. 1 and FIG. 4, the insecticidal lamp 6 electrically connected to the accumulator battery 34 through the control switch is provided on the support rod 2 below the first worm gear 22. The controller 5 is respectively connected to the control switch and the insecticidal lamp 6. The insecticidal lamp 6 includes the circular base 62 and the lamp cover 63, which are provided on the support rod 2 through the connection rods 61. The glass lampshade 64 is mounted between the circular base 62 and the lamp cover 63. The high-voltage electric fence 65 electrically connected to the accumulator battery by the control switch is provided outside the glass lampshade 64. The cylindrical circuit board 66 is provided inside the glass lampshade 64.

The cylindrical circuit board 66 includes the plurality of annular circuit boards 661 each having a unique ID. The plurality of light beads 6611 having a single-band spectrum are mounted on the annular circuit boards 661. The spectrums of the light beads 6611 on the same annular circuit board 661 are identical. The spectrums of the light beads 6611 not on the same annular circuit boards 661 are different to one another.

By configuring the insecticidal lamp 6 with different spectrums, the preferred bands for the pests appearing in different time periods are selectively opened, so as to improve the killing efficiency of the insecticidal lamp.

In one embodiment of the present invention, the swing cantilever 23 is the fourth motor-driven push rod connected to the controller 5 and the accumulator battery. The number of the distance measuring laser sensors 231 is one less than the number of the telescopic sections of the fourth motor-driven push rod. The telescopic section of maximum diameter of the fourth motor-driven push rod has a shorter length than the other telescopic sections, and the lengths of the other telescopic sections are equal to one another. Except for the telescopic section of maximum diameter, the other telescopic sections are each provided with one distance measuring laser sensor 231, and the distance measuring laser sensor 231 is located on the end portion of the telescopic section near the next telescopic section of reduced diameter. When the length of the fourth motor-driven push rod comes to be minimum, the fourth motor-driven push rod is located inside the electric element installation casing 3.

Since the swing cantilever 23 is configured with the above-mentioned structure, the swing cantilever 23 and all the distance measuring laser sensors 231 can be stored inside the electric element installation casing 3 when there is no need to collect the crop height, so that the man-made damage to the swing cantilever 23 and the damage to the swing cantilever 23 due to wind can be avoided, thereby prolonging the service life of the swing cantilever 23 and the distance measuring laser sensors 231.

In the present invention, a monitoring method of an IoT-based crop growth monitoring device is further provided, which includes the following steps.

S1. The current time is acquired, and whether the current time is the crop growth monitoring time point is determined. If yes, the first motor-driven push rod 37 is started to drive the top surface of the lower conical cover 32 to move until the position lower than the lowermost point of the swing cantilever 23, then go to the step S2 and step S7 at the same time; otherwise, continue to perform the step S1.

S2. The first motor 35 is started to drive the swing cantilever 23 to rotate by the predetermined angle, and the distances between all the distance measuring laser sensors 231 and the crops are collected by the distance measuring laser sensors 231 on the swing cantilever 23.

S3. Whether the total rotation angle (the accumulated rotation angle of the swing cantilever 23 during the process of the crop growth monitoring time point at the spot) of the swing cantilever 23 driven by the first motor 35 is greater than or equal to 360° is determined. If yes, go to step S4; otherwise go back to the step S2.

S4. The controller 5 calculates the average plant height of the crops according to all data sent back by the distance measuring laser sensors 231 during the startup process of the first motor 35, and sends the average plant height to the server.

S5. The server determines whether the difference between the average plant height uploaded by each controller 5 and the height threshold is less than the predetermined threshold. If yes, retain the average plant height, and go to the step S6; otherwise, mark the plant height as abnormal, and go to the step S17.

S6. After the determinations for all the average plant heights sent by the controller 5 are completed, and an average value of all the retained average plant heights is used as the measured plant height of the crops.

S7. The first motor-driven push rod 37 is controlled to drive the lower conical cover 32 to continue to move downward until traveling over the predetermined distance.

S8. The second motor 36 is started to drive the ultra-high-definition camera 26 to rotate by the predetermined angle, and then the second motor 36 is stopped. The ultra-high-definition camera 26 is started to capture the image of the crops.

S9. Whether the total rotation angle (the accumulated rotation angle of the ultra-high-definition camera 26 during the process of the crop growth monitoring time point at the spot) of the ultra-high-definition camera 26 driven by the second motor 36 is greater than or equal to 360° is determined. If yes, start up the first motor-driven push rod 37 to drive the lower conical cover 32 to return to the original position, and then go to the step S10; otherwise go back to the step S8.

S10. The controller 5 sends all the crop images captured by the ultra-high-definition camera 26 during the startup process of the second motor 36 to the server.

S11. The server inputs all the crop images into the three dimensional (3D) convolutional neural network for recognizing the pests and diseases, the 3D convolutional neural network for recognizing the yellow leaves, and the 3D convolutional neural network for recognizing the leaf areas, respectively, and outputs the types of the pests and diseases recognized from the crop images in presence of the pests and diseases, the confidence level of the crop images in presence of yellow leaves, and the confidence level of the leave area of each crop image.

The three 3D convolutional neural networks in step S11 are all 3D convolutional neural networks trained by the input corresponding pictures.

S12. When 30% of the crop images are in presence of the pests and diseases, go to the step S13. When the confidence level of 30% of the crop images is greater than the predetermined threshold, go to the step S14.

S13. According to the type of the corresponding pests in the crop images, the activity time and the preferred band of the peats are read and sent to the controller 5, and then the controller 5 controls the insecticidal lamp 6 to activate the light beads 6611 having the corresponding band during the activity time of the pests.

S14. All the salinity, humidity and PH values of the soil collected by the soil sensor 12 from the previous crop growth monitoring time point to the current crop growth monitoring time point are read to determine the cause of the yellow leaves of the crops.

S15. The average confidence level of the leaf areas is calculated by using the confidence levels of the leaf areas of the crop images uploaded by the same controller 5, and then whether the average confidence level of the leaf areas is greater than the predetermined confidence level is determined. If yes, retain the average confidence level of the leaf areas and go to the step S16; otherwise, delete the average confidence level of the leaf areas.

S16. When the number of the retained average confidence level of the leaf areas is greater than 70% of the total average confidence level of the leaf areas, the leaf areas of the crops are considered to be in a normal condition.

S17. According to the image corresponding to the abnormal plant height uploaded by the controller 5, the server determines whether the lodging phenomenon of the crops exists.

S18. According to the measured plant height, the pest condition, the yellow leaf condition, the leaf area and the lodging phenomenon of the crops, the comprehensive growth condition of the crops at the current crop growth monitoring time point is obtained.

When implementing the solution, preferably, the monitoring method of the IoT-based crop growth monitoring device further includes the following steps.

A1. The controller 5 receives the illumination intensity uploaded by the light sensor 42.

A2. When the light intensity is greater than the predetermined light intensity, the orientation of the sun at the current moment is determined.

A3. Whether the orientation of the solar cell panel 4 is identical to the orientation of the sun is determined. If yes, go back to the step A1; otherwise, go to the step A4.

A4. The elongation of the second motor-driven push rod 38 or the third motor-driven push rod 39 is adjusted according to the orientation of the sun so that the solar cell panel 4 faces toward the sun, and then go back to the step A1.

When implementing the solution, preferably, the monitoring method of the IoT-based crop growth monitoring device further includes the following steps.

B1. The rainfall amount uploaded by the rainfall sensor 41 is read.

B2. When the rainfall amount is greater than the predetermined rainfall amount, the second motor-driven push rod 38 and the third motor-driven push rod 39 are adjusted until the elongations of the second motor-driven push rod and the third motor-driven push rod are the same.

B3. Whether the lower conical cover 32 is snap-fitted with the upper conical cover 31 is determined according to the elongation of the first motor-driven push rod 37. If yes, go back to the step B1; otherwise go to the step B4.

B4. The first motor-driven push rod 37 is started to drive the lower conical cover 32 to move upward until the elongation of the first motor-driven push rod 37 reaches the predetermined elongation, and then go back to the step B1.

When the swing cantilever 23 is a motor-driven push rod, before the distance measuring laser sensors 231 start to collect data, the fourth motor-driven push rod is first controlled to stretch until a maximum elongation; when the first motor 35 drives the swing cantilever 23 to rotate by 360°, the fourth motor-driven push rod is started to retract until the minimum length.

What is claimed is:

1. An IoT-based crop growth monitoring device, comprising: a plurality of crop monitoring mechanisms mounted in a field; each of the crop monitoring mechanisms comprises a base and a support rod fixed on the base; a plurality of fixing elements obliquely extending downward and forming a fixing claw are fixedly mounted on the base; a plurality of soil sensors are fixed on the fixing elements;

an upper conical cover with an opening facing downward is fixed on an upper end of the support rod; a lower conical cover is movably mounted on the support rod below the upper conical cover; the lower conical cover is configured to slide up and down relative to the support rod; the lower conical cover is snap-fitted with the upper conical cover to form an electric element installation casing; a top surface of the support rod is connected to a solar cell panel having a top area larger than a maximum cross-sectional area of the electric element installation casing; a rainfall sensor and a light sensor are mounted on a top of the solar cell panel;

a first worm gear is mounted on the support rod at a position near a lowermost surface of the upper conical cover through a bearing; a mounting block is fixed on an upper surface of the first worm gear; a swing cantilever perpendicular to the support rod is fixed on the mounting block; a plurality of distance measuring laser sensors equidistantly arranged are mounted on a lower surface of the swing cantilever; a strip-shaped groove for holding the swing cantilever is provided on an edge of the lower conical cover; a second worm gear is mounted on the support rod at a position near a top surface of the upper conical cover through a bearing; a support block is fixed on an upper surface of the second worm gear; an ultra-high-definition camera is obliquely mounted on the support block through a connection rod, and a lowermost point of the ultra-high-definition camera is higher than an uppermost point of the swing cantilever;

a support plate is fixed on the support rod in the electric element installation casing; an accumulator battery, a first motor connected to the accumulator battery, a second motor and a first motor-driven push rod are placed on the support plate; a first worm and a second worm are respectively fixed on output shafts of the first motor and the second motor; the first worm is engaged with the first worm gear, and the second worm is engaged with the second worm gear; a free end of the first motor-driven push rod is fixedly connected to an inner surface of the lower conical cover; an uppermost point of the support plate for mounting the first motor-driven push rod is lower than a lowermost point of the swing cantilever; and the distance measuring laser sensors and the ultra-high-definition camera are all electrically connected to the accumulator battery; the solar cell panel is connected to the accumulator battery and a controller through a solar controller; the soil sensors, the rainfall sensor, the light sensor, the distance measuring laser sensors, the first motor, the second motor, the ultra-high-definition camera and the accumulator battery are all connected to the controller located in the electric element installation casing; and the controllers of all the crop monitoring mechanisms communicate with a server in a monitor room through a wireless network.

2. The IoT-based crop growth monitoring device according to claim 1, wherein the solar cell panel is movably mounted on a top end of the support rod through a spherical hinge; a second motor-driven push rod and a third motor-driven push rod are fixed on the support plate inside the electric element installation casing; connection lines between the second motor-driven push rod and the support rod, and between the third motor-driven push rod and the support rod are perpendicular to each other; free ends of the second motor-driven push rod and the third motor-driven push rod both protrude out of the upper conical cover and are connected to the solar cell panel by spherical hinges; and when the solar cell panel is placed horizontally, the second motor-driven push rod and the third motor-driven push rod are in a stretched state.

3. The IoT-based crop growth monitoring device according to claim 1, wherein an insecticidal lamp electrically connected to the accumulator battery through a control switch is provided on the support rod below the first worm gear; the controller is respectively connected to the control switch and the insecticidal lamp; the insecticidal lamp comprises a circular base and a lamp cover, the circular base and the lamp cover are provided on the support rod through connection rods; a glass lampshade is mounted between the circular base and the lamp cover; a high-voltage electric fence electrically connected to the accumulator battery by the control switch is provided outside the glass lampshade; and a cylindrical circuit board is provided inside the glass lampshade; and the cylindrical circuit board comprises a plurality of annular circuit boards each having a unique ID; a plurality of light beads having a single-band spectrum are mounted on the annular circuit boards; spectrums of the light beads on a same annular circuit board are identical; spectrums of the light beads not on the same annular circuit board are different.

4. The IoT-based crop growth monitoring device according to claim 1, wherein the soil sensors comprise soil salt content sensors, pH probes, and humidity sensors; and the soil salt content sensors, the pH probes, and the humidity sensors are electrically connected to the controller.

5. The IoT-based crop growth monitoring device according to claim 1, wherein the swing cantilever is a fourth motor-driven push rod connected to the controller and the accumulator battery; a number of the distance measuring laser sensors is one less than a number of telescopic sections of the fourth motor-driven push rod; a telescopic section of a maximum diameter of the fourth motor-driven push rod has a shorter length than other telescopic sections, and lengths of the other telescopic sections are equal to one another; except for the telescopic section of the maximum diameter, the other telescopic sections are each provided with one distance measuring laser sensor, and the distance measuring laser sensor is located on an end portion of the telescopic section near a next telescopic section of a reduced diameter; when a length of the fourth motor-driven push rod comes to be minimum, the fourth motor-driven push rod is located inside the electric element installation casing.

6. A monitoring method of the IoT-based crop growth monitoring device according to claim 1, comprising:
   S1. acquiring a current time, and determining whether the current time is a crop growth monitoring time point, if yes, starting up the first motor-driven push rod to drive a top surface of the lower conical cover to move until a position lower than the lowermost point of the swing cantilever, then going to step S2 and step S7 at the same time, otherwise, continuing to perform step S1;
   S2. starting the first motor to drive the swing cantilever to rotate by a predetermined angle, and collecting distances between the distance measuring laser sensors and crops by all the distance measuring laser sensors on the swing cantilever one time;
   S3. determining whether a total rotation angle of the swing cantilever driven by the first motor is greater than or equal to 360°, if yes, going to step S4, otherwise, going back to step S2;
   S4. calculating an average plant height of the crops, by the controller, according to all data sent back by the distance measuring laser sensors during a startup process of the first motor, and sending the average plant height of the crops to the server;
   S5. determining, by the server, whether a difference between an average plant height uploaded by each controller and a height threshold is less than a predetermined threshold, if yes, retaining the average plant height, and going to step S6, otherwise, marking the average plant height as abnormal, and going to step S17;
   S6. using an average value of all retained average plant heights as a measured plant height of the crops when determinations for all the average plant heights uploaded by the controller are completed;
   S7. controlling the first motor-driven push rod to drive the lower conical cover to continue to move downward until traveling over a predetermined distance;
   S8. starting up the second motor to drive the ultra-high-definition camera to rotate by a predetermined angle; stopping the second motor, and starting up the ultra-high-definition camera to capture crop images;

S9. determining whether a total rotation angle of the ultra-high-definition camera driven by the second motor is greater than or equal to 360°, if yes, starting up the first motor-driven push rod to drive the lower conical cover to return back to an original position, and then going to step S10; otherwise, going back to step S8;

S10. sending, by the controller, all the crop images captured by the ultra-high-definition camera during a startup process of the second motor to the server;

S11. inputting, by the server, all the crop images into a three dimensional (3D) convolutional neural network for recognizing pests and diseases, a 3D convolutional neural network for recognizing yellow leaves, and a 3D convolutional neural network for recognizing a leaf area, respectively, and outputting types of the pests and diseases recognized from the crop images in presence of the pests and diseases, a confidence level of the crop images in presence of the yellow leaves, and a confidence level of leave area of each crop image;

S12. when 30% of the crop images are in presence of the pests and diseases, going to step S13; and when the confidence level of 30% of the crop images is greater than the predetermined threshold, going to the step S14;

S13. reading an activity time and a preferred band of the peats according to the type of the corresponding pests in the crop images, sending the activity time and the preferred band of the peats to the controller, and controlling the insecticidal lamp by the controller to activate the light beads having the preferred band during the activity time of the pests;

S14. reading all salinity, humidity and PH values of soil collected by the soil sensors from a previous crop growth monitoring time point to a current crop growth monitoring time point to determine a cause of the yellow leaves of the crops;

S15. calculating an average confidence level of the leaf areas by using the confidence levels of the leaf areas of the crop images uploaded by the same controller; and determining whether the average confidence level of the leaf areas is greater than a predetermined confidence level; if yes, retaining the average confidence level of the leaf areas and going to step S16; otherwise, deleting the average confidence level of the leaf areas;

S16. considering the leaves of the crops to be in a normal condition when a number of the retained average confidence level of the leaf areas is greater than 70% of a total average confidence level of the leaf areas;

S17. determining, by the server, whether a lodging phenomenon of the crops exists according to the crop images of abnormal plant heights uploaded by the controller; and S18. obtaining a comprehensive growth condition of the crops at the current crop growth monitoring time point according to the measured plant height, a pest condition, a yellow leaf condition, the leaf area and the lodging phenomenon of the crops.

7. The monitoring method of the IoT-based crop growth monitoring device according to claim 6, further comprising:

A1: receiving, by the controller, a light intensity uploaded by the light sensor;

A2: determining an orientation of the sun at a current moment when the light intensity is greater than a predetermined light intensity;

A3: determining whether an orientation of the solar cell panel is identical to the orientation of the sun; if yes, go to step A1; otherwise, go to step A4; and A4: adjusting an elongation of the second motor-driven push rod or the third motor-driven push rod according to the orientation of the sun to make the solar cell panel faces toward the sun, and then go back to step A1.

8. The monitoring method of the IoT-based crop growth monitoring device according to claim 6, further comprising:

B1: reading a rainfall amount uploaded by the rainfall sensor;

B2: adjusting the second motor-driven push rod and the third motor-driven push rod until the elongations of the second motor-driven push rod and the third motor-driven push rod are the same when the rainfall amount is greater than a predetermined rainfall amount;

B3: determining whether the lower conical cover is snap-fitted with the upper conical cover according to an elongation of the first motor-driven push rod; if yes, going back to step B1;

otherwise, going to step B4; and

B4: starting up the first motor-driven push rod to drive the lower conical cover to move upward until the elongation of the first motor-driven push rod reaches a predetermined elongation; and then going back to step B1.

9. The monitoring method of the IoT-based crop growth monitoring device according to claim 6, wherein when the swing cantilever is a motor-driven push rod, before the distance measuring laser sensors start to collect data, the fourth motor-driven push rod is first controlled to stretch until a maximum elongation; when the first motor drives the swing cantilever to rotate by 360°, the fourth motor-driven push rod is started to retract until a minimum length.

10. The IoT-based crop growth monitoring device according to claim 2, wherein the swing cantilever is a fourth motor-driven push rod connected to the controller and the accumulator battery; a number of the distance measuring laser sensors is one less than a number of telescopic sections of the fourth motor-driven push rod; a telescopic section of a maximum diameter of the fourth motor-driven push rod has a shorter length than other telescopic sections, and lengths of the other telescopic sections are equal to one another; except for the telescopic section of the maximum diameter, the other telescopic sections are each provided with one distance measuring laser sensor, and the distance measuring laser sensor is located on an end portion of the telescopic section near a next telescopic section of a reduced diameter; when a length of the fourth motor-driven push rod comes to be minimum, the fourth motor-driven push rod is located inside the electric element installation casing.

11. The IoT-based crop growth monitoring device according to claim 3, wherein the swing cantilever is a fourth motor-driven push rod connected to the controller and the accumulator battery; a number of the distance measuring laser sensors is one less than a number of telescopic sections of the fourth motor-driven push rod; a telescopic section of a maximum diameter of the fourth motor-driven push rod has a shorter length than other telescopic sections, and lengths of the other telescopic sections are equal to one another; except for the telescopic section of the maximum diameter, the other telescopic sections are each provided with one distance measuring laser sensor, and the distance measuring laser sensor is located on an end portion of the telescopic section near a next telescopic section of a reduced diameter; when a length of the fourth motor-driven push rod comes to be minimum, the fourth motor-driven push rod is located inside the electric element installation casing.

12. The IoT-based crop growth monitoring device according to claim 3, wherein the swing cantilever is a fourth motor-driven push rod connected to the controller and the accumulator battery; a number of the distance measuring laser sensors is one less than a number of telescopic sections of the fourth motor-driven push rod; a telescopic section of a maximum diameter of the fourth motor-driven push rod has a shorter length than other telescopic sections, and lengths of the other telescopic sections are equal to one another; except for the telescopic section of the maximum diameter, the other telescopic sections are each provided with one distance measuring laser sensor, and the distance measuring laser sensor is located on an end portion of the telescopic section near a next telescopic section of a reduced diameter; when a length of the fourth motor-driven push rod comes to be minimum, the fourth motor-driven push rod is located inside the electric element installation casing.

13. The IoT-based crop growth monitoring device according to claim 4, wherein the swing cantilever is a fourth motor-driven push rod connected to the controller and the accumulator battery; a number of the distance measuring laser sensors is one less than a number of telescopic sections of the fourth motor-driven push rod; a telescopic section of a maximum diameter of the fourth motor-driven push rod has a shorter length than other telescopic sections, and lengths of the other telescopic sections are equal to one another; except for the telescopic section of the maximum diameter, the other telescopic sections are each provided with one distance measuring laser sensor, and the distance measuring laser sensor is located on an end portion of the telescopic section near a next telescopic section of a reduced diameter; when a length of the fourth motor-driven push rod comes to be minimum, the fourth motor-driven push rod is located inside the electric element installation casing.

14. The monitoring method of the IoT-based crop growth monitoring device according to claim 6, wherein the solar cell panel is movably mounted on a top end of the support rod through a spherical hinge; a second motor-driven push rod and a third motor-driven push rod are fixed on the support plate inside the electric element installation casing; connection lines between the second motor-driven push rod and the support rod, and between the third motor-driven push rod and the support rod are perpendicular to each other; free ends of the second motor-driven push rod and the third motor-driven push rod both protrude out of the upper conical cover and are connected to the solar cell panel by spherical hinges; and when the solar cell panel is placed horizontally, the second motor-driven push rod and the third motor-driven push rod are in a stretched state.

15. The monitoring method of the IoT-based crop growth monitoring device according to claim 6, wherein an insecticidal lamp electrically connected to the accumulator battery through a control switch is provided on the support rod below the first worm gear; the controller is respectively connected to the control switch and the insecticidal lamp; the insecticidal lamp comprises a circular base and a lamp cover, the circular base and the lamp cover are provided on the support rod through connection rods; a glass lampshade is mounted between the circular base and the lamp cover; a high-voltage electric fence electrically connected to the accumulator battery by the control switch is provided outside the glass lampshade; and a cylindrical circuit board is provided inside the glass lampshade; and the cylindrical circuit board comprises a plurality of annular circuit boards each having a unique ID; a plurality of light beads having a single-band spectrum are mounted on the annular circuit boards; spectrums of the light beads on the same annular circuit board are identical; spectrums of the light beads not on the same annular circuit board are different.

16. The monitoring method of the IoT-based crop growth monitoring device according to claim 6, wherein the soil sensors comprise soil salt content sensors, pH probes, and humidity sensors; and the soil salt content sensors, the pH probes, and the humidity sensors are electrically connected to the controller.

17. The monitoring method of the IoT-based crop growth monitoring device according to claim 6, wherein the swing cantilever is a fourth motor-driven push rod connected to the controller and the accumulator battery; a number of the distance measuring laser sensors is one less than a number of telescopic sections of the fourth motor-driven push rod; a telescopic section of a maximum diameter of the fourth motor-driven push rod has a shorter length than other telescopic sections, and lengths of the other telescopic sections are equal to one another; except for the telescopic section of the maximum diameter, the other telescopic sections are each provided with one distance measuring laser sensor, and the distance measuring laser sensor is located on an end portion of the telescopic section near a next telescopic section of a reduced diameter; when a length of the fourth motor-driven push rod comes to be minimum, the fourth motor-driven push rod is located inside the electric element installation casing.

\* \* \* \* \*